United States Patent [19]

Spitz

[11] 3,989,380
[45] Nov. 2, 1976

[54] APPARATUS FOR DETECTING FLAWS IN TRANSPARENT CONTAINERS

[75] Inventor: Tibor Spitz, Montreal, Canada

[73] Assignee: Dominion Glass Company Limited, Montreal, Canada

[22] Filed: Apr. 14, 1975

[21] Appl. No.: 567,980

[30] Foreign Application Priority Data
Apr. 2, 1975 Canada .................................. 223704

[52] U.S. Cl. .................................. 356/32; 356/198; 356/240; 356/244
[51] Int. Cl.² .................. G01B 11/16; G01N 21/16
[58] Field of Search ................ 356/32, 33, 114, 115, 356/119, 198, 239, 240, 244; 250/223 B

[56] References Cited
UNITED STATES PATENTS

| | | | |
|---|---|---|---|
| 1,934,187 | 11/1933 | Glasgow et al. | 356/33 |
| 2,593,311 | 4/1952 | Johnson et al. | 356/240 |
| 3,790,285 | 2/1974 | Swinson | 356/33 |

*Primary Examiner*—Vincent P. McGraw

[57] ABSTRACT

A method and apparatus are provided for testing containers such as glass bottles. The container is filled with an opaque material and then immersed in a bath having two parallel walls of light transmitting material. The bath contains a light transmitting liquid having a refractive index comparable with that of the material of the container and a light transmitting efficiency different from that of the material of the container. Light is projected through the parallel walls of the bath to illuminate the walls of the container so that the wall thickness is clearly visible and the distribution of wall thickness can be studied.

2 Claims, 7 Drawing Figures

APPARATUS FOR DETECTING FLAWS IN TRANSPARENT CONTAINERS

This invention relates to a method of testing containers made from light-transmitting material to determine physical properties and characteristics of the articles immediately after manufacture of the articles.

For the sake of convenience, the following description will be directed primarily to bottles and the like made of glass. However, it is intended that the description should be directed to containers generally made of any light transmitting material. Accordingly, such an interpretation should be given to all aspects of the description where glass bottles are used in exemplary fashion.

When manufacturing glass bottles, the bottles are made on a continuous basis and it is necessary to control the manufacture to avoid a high rejection rate at the end of the manufacturing process. Accordingly, it would be desirable to be able to check some of the more important characteristics of a bottle by removing the bottle off the production line, testing the bottle immediately and quickly, and then making any necessary corrections to the manufacturing process based on defects found in the tested bottle.

At the present time, bottle testing is done by removing a sample bottle, annealing the bottle, and then cutting the bottle to obtain ring sections of the bottle. Each ring section is then tested individually for characteristics such as wall thickness, the presence of cord and striae, roundness and similar properties. Such a procedure is time consuming particularly because of the annealing process. Consequently if the tested bottle is faulty it may be necessary to scrap a large number of bottles which have been manufactured while the test bottle was annealed.

It has been found that a container such as a glass bottle can be tested relatively quickly for wall distribution without first annealing and cutting the container. Accordingly, in one of its aspects the present invention provides a method of testing containers of a light transmitting material, the method comprising the steps: filling the container with an opaque material; immersing the container in a bath having two parallel walls of light transmitting material and containing a light transmitting liquid, the liquid having a refractive index comparable with that of the material of the container and a light transmitting efficiency different from that of the material of the container; and projecting light through the parallel walls of the bath to illuminate the wall of the container to thereby make the wall thickness clearly visible whereby the distribution of wall thickness can be studied.

It has also been found that the foregoing method can be used as a basis for qualitative analysis of the material of the container. Accordingly, in another of its aspects the present invention provides a method of testing containers of light transmitting material, the method comprising the steps: filling the container with an opaque material; immersing the container in a bath having two parallel walls of light transmitting material and containing a light transmitting liquid, the liquid having a refractive index comparable with that of the material of the container and a light transmitting efficiency different from that of the material of the container projecting polarized light through the parallel walls of the bath to illuminate the wall of the container; and analysing light transmitted through selected portions of the cross wall of the container using an optical compensator at the other said of the bath from the light source whereby the presence of cord and striae can be detected qualitatively.

In another of its aspects the invention provides apparatus for use in testing containers of a light transmitting material and filled with an opaque material. The apparatus includes a bath having a pair of parallel light transmitting walls and adapted to contain a light transmitting liquid of a refractive index comparable with that of the material of the container and having a light transmitting efficiency different from that of the material of the container, and a light source positioned for projecting light through the parallel walls and through the liquid so that upon placing the container in the liquid, the wall thickness distribution can be inspected by viewing the projected light from a side of the tank remote from the light source.

These and other aspects of the invention will be better understood with reference to the drawings, in which.

Figure 1:
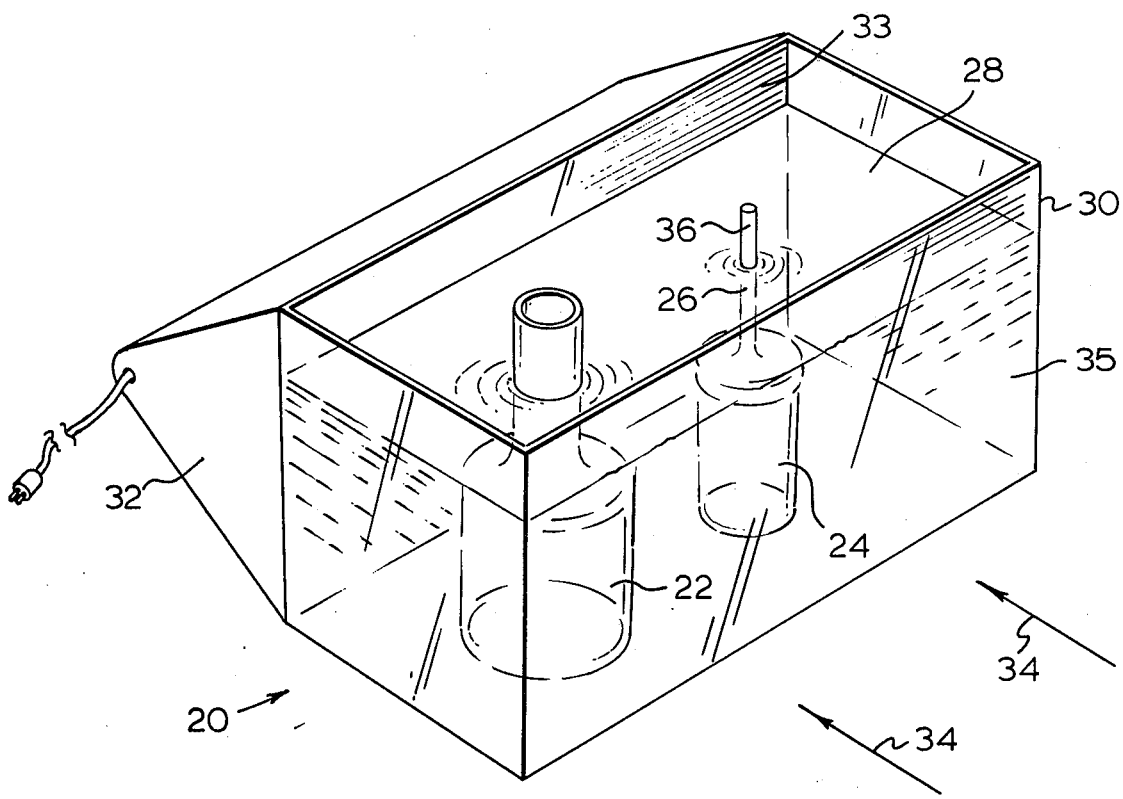
FIG. 1 is a perspective view from above a piece of apparatus according to the invention for practising a method of testing according to the invention.

Reference is first made to FIG. 1 which illustrates apparatus 20 containing two clear glass containers 22 and 24, the latter of which has a cap 26. The containers are immersed in a light-transmitting liquid 28 contained in a glass-walled bath 30, and a light box 32 is located adjacent one of a pair of parallel walls 33, 35 of the rectangular bath.

The liquid 28 has a refractive index which is as near as possible the same as that of the material of the containers 22, 24 in the bath 30. Also, the light transmitting efficiency (i.e., percentage of light transmitted by unit thickness) is different from that of the container material. The reasons for these criteria will be discussed later.

The light box projects light through the bath towards a viewer looking in the direction of the arrows 34. The containers 22, 25 are filled with an opaque material. This material could be a powder, a naturally opaque liquid, a coloured liquid, or more conveniently the same liquid 28 with a dye added to make the liquid opaque. Container 22 is sufficiently tall that it projects from the liquid 28 and can be rotated for viewing whereas the container 24 is rotated by using an extension 36 of cap 26 to permit the container to be rotated from outside the liquid 28.

Figure 2:
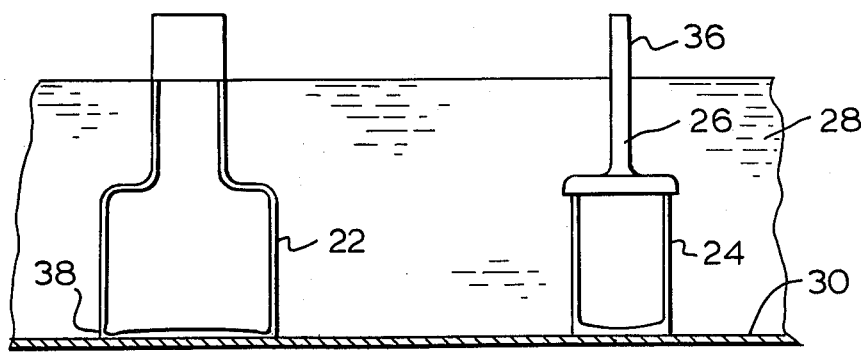
FIG. 2 is a view illustrating wall distribution of containers in the apparatus shown in FIG. 1.

To use the apparatus 20, the light box 32 is activated to project light through the bath 30. Preferably, the interface between the box and the bath 30 includes an optical diffuser so that a person looking in the direction of the arrows 34 sees a bright white or coloured background behind the containers 22, 24. When this person looks at the containers he will see the container walls outlined distinctly as shown in FIG. 2. The reasons for the distinct wall outline willl be described with reference to FIGS. 3 to 5.

As seen in FIG. 2, the container 22 has a thin wall at a point indicated by the numeral 28. All diametric cross-sections of the container 22 can be studied by simply rotating the container about its vertical axis and viewing the wall thickness as the container is rotated. In the event that the wall thinning at 38 is unacceptable in the selected section shown then this would indicate that a problem exists in the manufacturing process. It is important to note that the container 22 has been removed from the production line and placed in the tank 30 without annealing the container. Consequently very quick checks on the wall thickness and wall distribution can be conducted in this manner and any necessary corrections made in the manufacturing process.

FIG. 2 also illustrates what the viewer would see when looking at container 24. In this view the bottom of the container is irregular and further cross-sections can be studied by rotating the container using the extension 36 of the cap 26.

An optical explanation of the results achieved with reference to FIGS. 1 and 2 will now be given with reference to FIGS. 3 to 5 which are purely diagrammatic.

Figure 3:
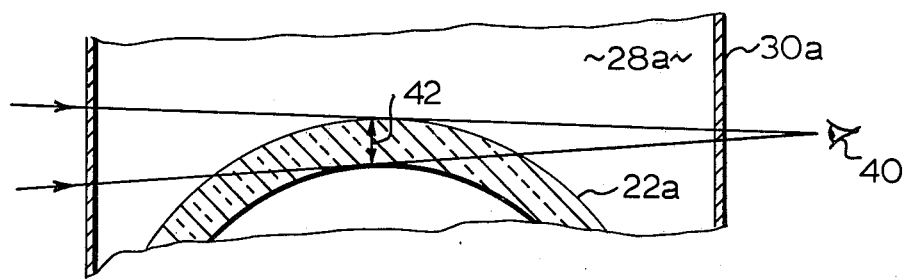
FIGS. 3 to 5 are diagrammatic illustrations of an observer's view of a test using the apparatus.

As seen in FIG. 3, a light transmitting liquid 28a is contained within a bath 30a and the liquid 28a surrounds the container 22a. The liquid and container have substantially the same refractive indices so that the light rays will not be refracted when they pass the interfaces between the liquid and the container.

A viewer 40 will see light passing through the liquid 28a but will be aware of a difference in light intensity where the light passes through the container 22a. This is because of the difference in light transmission efficiency between the liquid 28a and the container 22a. Where the light travels through the container it will appear slightly brighter than where it travels through the liquid and consequently the width of the container at this point will be seen to be equal to that of the arrow 42. Any light which passes through the wall of the container 22a and into the opaque material within the container will be lost and will not be seen by the viewer 40. Because the light rays passing to the viewer 40 have not been refracted, the viewer will see a thickness of all which is substantially the true wall thickness.

Figure 4:
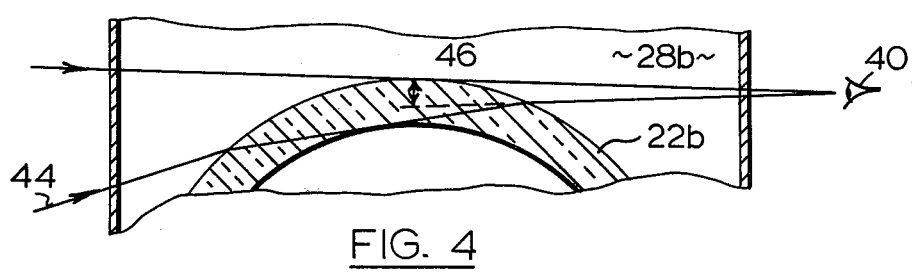

Turning now to FIG. 4, in this figure liquid 28b has a refractive index smaller than that of a container 22b. Consequently, a light ray 44 entering the container 22b will be refracted and will again be refracted when it leaves the container 22b. The viewer 40 now sees an image 46 which is smaller than the thickness of the wall of the container 22b.

Figure 5:
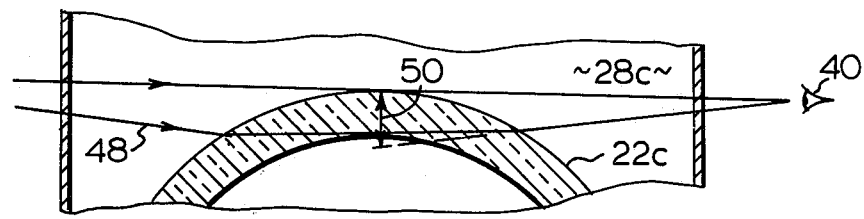

FIG. 5 illustrates a condition in which liquid 28c has a larger refractive index than that of a container 22c. A ray 48 is refracted in a manner which results in an image 50 which is larger than the true thickness of the wall of the container 22c.

It will be evident from a comparison of FIGS. 3 to 5 that the liquid can be chosen to give a magnified image, to give a diminished image, or to give a substantially true view of the thickness. Which liquid is used will depend upon the refractive index of the container being studied and to some extent upon a subjective preference by the operator. In any event the chosen liquid exhibits a different light transmitting efficiency from that of the container material so that the viewer will see the container wall easily. There will be a relationship between the light transmitting qualities of the container, the liquid, the length of the light path through the liquid, and also between the colours of the light, the liquid and the container. However, it is a simple matter to choose the materials and light intensity to achieve the desired result without undue experimentations.

The liquid 28 (FIG. 1) can have any refractive index which is comparable to that of the container material. In this sense the word "comparable" is used to mean "similar within close limits." It will be evident to an operator if he uses a liquid which has a refractive index substantially different from that of the container material because aberration of the image will occur. Although no specific range can be defined because of the subjective nature of the results, the best results will occur when the container material and the liquid have the same refractive indices and different light transmission efficiencies.

Suitable attachments such as cap 26 can be used for any container which is otherwise submerged in the liquid. Also if the neck of container 22 is to be studied, an adaptor or cap can be attached so that the container can be inverted.

Figure 6:
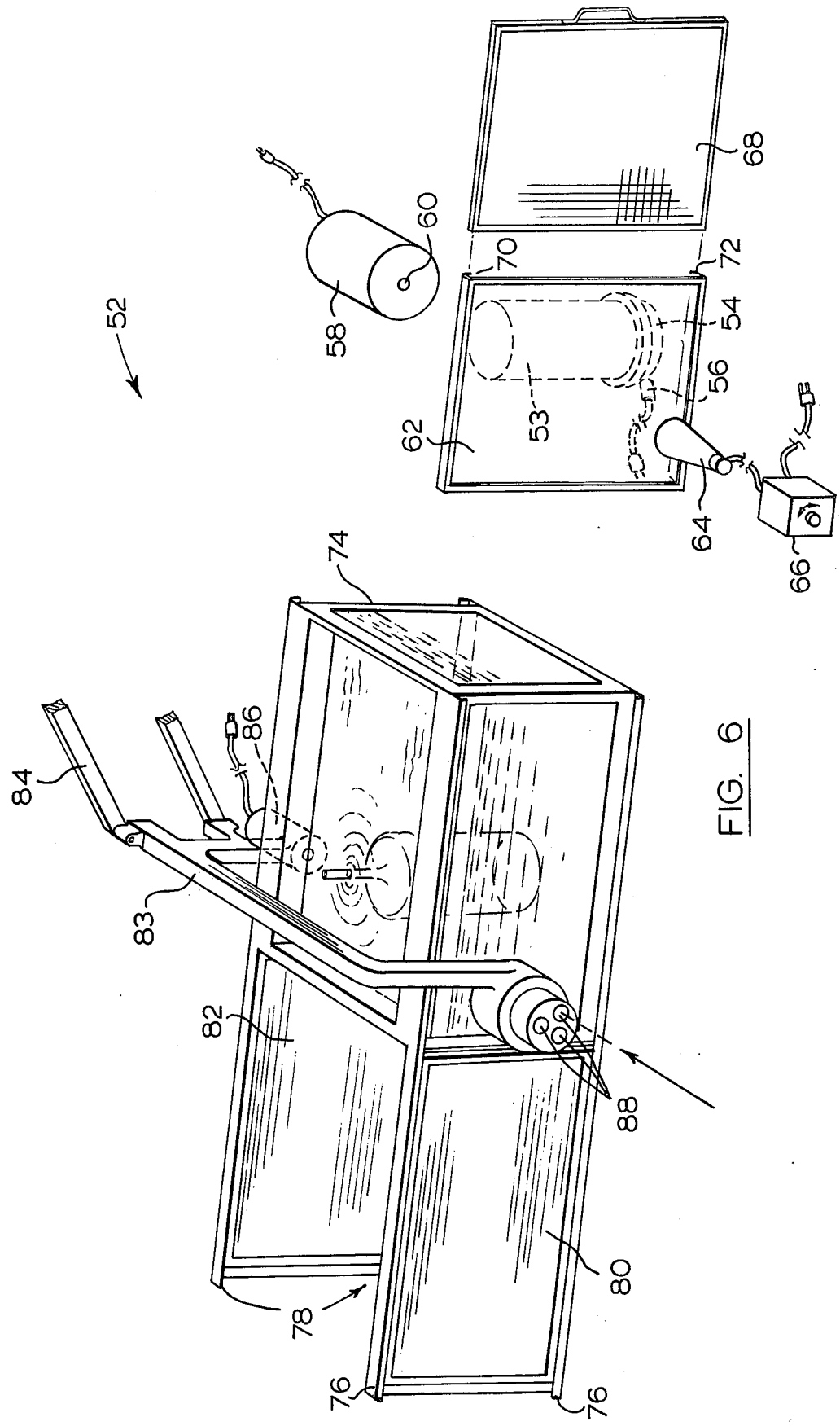
FIG. 6 is a perspective view of another embodiment of the invention for testing more physical properties of a container.

Reference is now made to FIG. 6 which illustrates apparatus 52 incorporating aspects of the invention and intended to conduct a more comprehensive series of tests than the apparatus illustrated in FIG. 1. However, the apparatus 52 incorporates the principle of operation of the apparatus 20 (FIG. 1) as will be described.

Apparatus 52 will be described with reference to a container 53 as it is passed through the tests conducted on apparatus 52. Initially, the container is placed on a turntable 54 which can be driven slowly by an electric motor 56 for viewing the container. The first test corresponds to that discussed in a paper given by Tibor Spitz and Eva Danickova published in 1969 in a Chechslovakian publication named "Sklar A. Keramik." The test consists of directing light from a source 58, which includes a condensor and an aperture 60, towards the container 53. Light is projected onto a diffuser screen 62 so that a viewer placed on the opposite side of the screen from the container 53 will see a shadow cast on the screen by the light source 58. As described in the aforementioned article, a further light source 64 combined with an auto-transformer 66 is used to compensate for the shadow. This is done by directing the light source 64 to produce a uniform distribution on the screen 62 until the shadow intensity substantially matches that about it on the remainder of the screen. At this point irregularities in the surface of the container are shown because they are of a denser shadow than the remainder of the container. This test then gives a qualitative analysis of the surface finish of the container.

Figure 7:
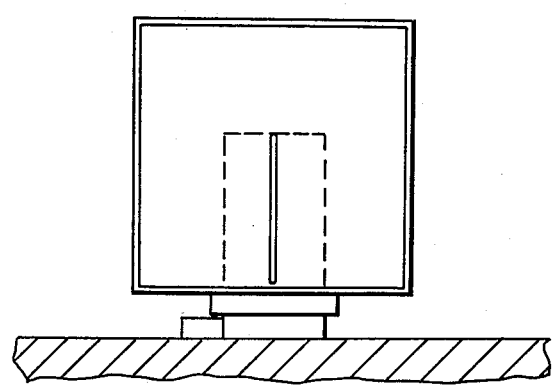
FIG. 7 is an observer's view of one of the tests conducted on the apparatus shown in FIG. 6.

The next test is also conducted on the turntable 54. The container 53 is filled with an opaque material which for convenience can be a liquid containing a dye. If the container 53 is cylindrical and is positioned from the screen 62 suitably, then light entering the container will be deflected by refraction towards a point on the screen. If the light from both sides meets the same point on the screen then the container is cylindrical as demonstrated in FIG. 7. It will be apparent that if the container differs in any way from cylindrical form, then the image on the screen will show this fact to the viewer.

A third test can also be conducted on the turntable 54. A transparent grid 68 can be placed adjacent the screen 62 in suitable upper and lower tracks 70, 72 and the projection of the container on the screen can be studied in relation to a desired shape shown either on the grid 68 or measured on the grid 68 from known dimensions. Further, as the turntable rotates, the container 52 can be checked to ensure that its vertical axis is in fact vertical with reference to the base of the container.

Next, the container is tested in bath 74 which is similar to the bath 30 described with reference to FIG. 1. However, in this case the bath 74 includes two pairs of runners 76, 78 which guide respective screens 80, 82 for placing adjacent opposite faces of the bath 74 as will be described. A generally U-shaped frame 83 is suspended from a pantograph arrangement 84 (part of which is shown) for movement of the frame 83 relative to the bath 74. A first leg of the frame 83 terminates in a light source 86 aligned with one of three oculars 88 mounted in a rotatable member in a corresponding end of the other leg of the frame 83. The oculars can be rotated to bring any one of them in line with the light source 86.

As drawn, the screen 82 is remote from the bath 74 and the next test is conducted by bringing this screen into a position where it substantially covers a portion of the bath adjacent the light source 86. It will be evident that the walls of the bath are transparent, and the screen is a diffuser so that the effect is to produce a test corresponding to that described with reference to FIG. 1. However, in this case the light source 86 includes a polarizer for subsequent use in another test. This will have no effect upon the viewing of wall distribution.

Once this wall distribution test is complete, the screen 82 is withdrawn into its original position and the container is tested for cord and striae. Various oculars 88 are provided but in fact any compensator can be used to view the polarized light emitted from the source 86. Because the container is filled with an opaque material, light passing through the wall of the container can be isolated readily and viewed through the ocular. By rotating the compensator, cord and striae can be analysed qualitatively and the container can be rotated for testing the various positions on the walls of the container. Here again, it was unnecessary to anneal the container and consequently quick results can be obtained to limit the expense of running a production line which may be producing unsatisfactory products.

A record of the test for wall distribution can be made by use of diffuser screen 80. The image of the walls is projected on to this screen to enable a photograph to be taken which records this result.

It will be apparent that the container can be of any light transmitting material and that the liquid in the tank can be chosen to have a corresponding refractive index. Where the container floats it can be weighted internally.

Tests were conducted using the invention applied to a typical glass container having a refractive index of 1.5135. Satisfactory results were obtained using the following liquids, in whch the refractive indices are shown in parenthesis: water (1.3330); ethyl-alcohol (1.3595); benzene (1.4986); dimethylphtalate (1.5135); nitrobenzene (1.5498); and mono-bromonaphtalene (1.6576).

Data on the refractive indices of the above materials were taken from "Aldrich Chemical Handbook, 1975–1976".

What I claim as my invention is:

1. A method of testing a container of a light transmitting material, the method comprising the steps: filling the container with an opaque material; immersing the container in a bath having two parallel walls of light transmitting material and containing a light transmitting liquid, the liquid having a refractive index comparable with that of the material of the container and a light transmitting efficiency different from that of the material of the container, and projecting light through the parallel walls of the bath to illuminate the walls of the container to thereby make the wall thickness clearly visible whereby the distribution of wall thickness can be studied.

2. A method of testing containers of light transmitting material, the method comprising the steps: filling the container with an opaque material; immersing the container in a bath having two parallel walls of light transmitting material and containing a light transmitting liquid, the liquid having a refractive index comparable with that of the material of the container and a light transmitting efficiency different from that of the material of the container; and projecting polarized light through the parallel walls of the bath to illuminate the wall of the container, and analysing the light transmitted through the wall thickness of the container using an optical compensator at the other side of the bath from the light source whereby the presence of cord and striae can be detected qualitatively.

* * * * *